United States Patent [19]

Samuels

[11] Patent Number: 4,696,396
[45] Date of Patent: Sep. 29, 1987

[54] HEMOSTATIC CLIP CARTRIDGE

[76] Inventor: Peter B. Samuels, 14708 Sutton St., Sherman Oaks, Calif. 91403

[21] Appl. No.: 22,576

[22] Filed: Mar. 9, 1987

Related U.S. Application Data

[63] Continuation of Ser. No. 810,581, Dec. 19, 1985, abandoned.

[51] Int. Cl.⁴ .................................................. B65D 85/16
[52] U.S. Cl. ........................................ 206/339; 206/340; 206/341; 227/DIG. 1
[58] Field of Search ............... 206/338, 339, 340, 341, 206/476, 477, 482; 227/DIG. 1

[56] References Cited

U.S. PATENT DOCUMENTS

| | | | |
|---|---|---|---|
| 3,270,745 | 9/1966 | Wood | 227/DIG. 1 |
| 3,326,216 | 6/1967 | Wood | 227/DIG. 1 |
| 3,363,628 | 1/1968 | Wood | 227/DIG. 1 |
| 3,439,522 | 4/1969 | Wood | 227/DIG. 1 |
| 3,439,523 | 4/1969 | Wood | 227/DIG. 1 |
| 3,713,533 | 1/1973 | Reimels | 227/DIG. 1 |
| 4,076,120 | 2/1978 | Carroll et al. | 206/339 |
| 4,146,130 | 3/1979 | Samuels et al. | 206/340 |
| 4,361,229 | 11/1982 | Mericle | 206/341 |
| 4,412,617 | 11/1983 | Cerwin | 206/63.3 |

*Primary Examiner*—Stephen Marcus
*Assistant Examiner*—Brenda J. Ehrhardt
*Attorney, Agent, or Firm*—Jones, Day, Reavis & Pogue

[57] ABSTRACT

An improved hemostatic clip cartridge wherein hemostatic clips are stored prior to use is disclosed. The cartridge, having a number of parallel walls defining individual clip compartments in which the clips are stored, is provided with outwardly extending channel members that extend into each clip compartment. The opposed channel members are positioned to releasably secure a clip therebetween. An applicator is provided so that an individual clip may be removed from its compartment without releasing the remaining clips.

5 Claims, 6 Drawing Figures

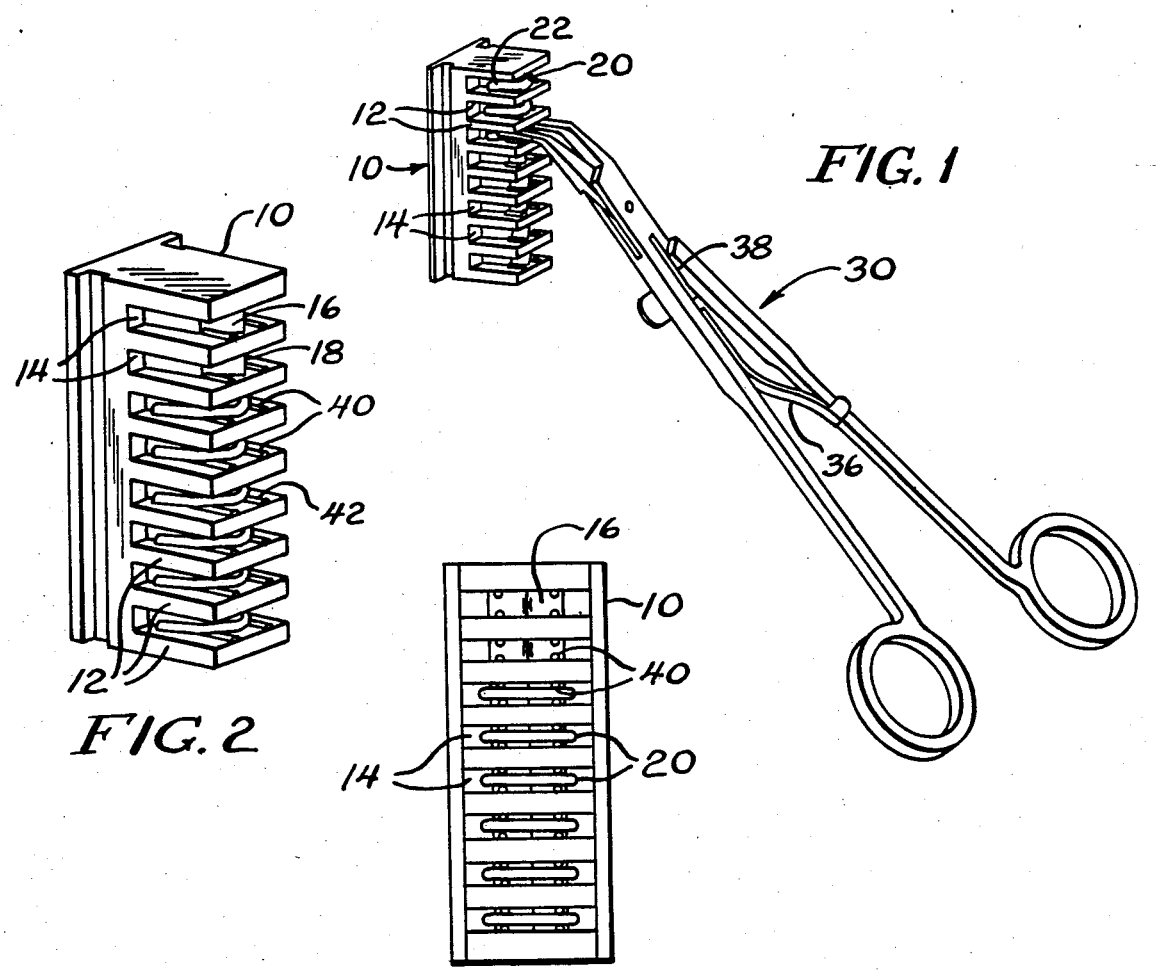

HEMOSTATIC CLIP CARTRIDGE

This application is a continuation of application of Ser. No. 810,581, filed Dec. 19, 1985, now abandoned.

BACKGROUND OF THE INVENTION

This invention relates to mechanisms useful in the strangulation of tubular members. Specifically, it is directed towards devices including hemostatic clip systems useful in the strangulation of blood vessels and other fluid ducts in the human body.

The particular application of this invention to the occlusion of blood vessels will serve as an illustration of the inventive concepts enclosed herein. It will be appreciated, however, that the mechanism embodying the concepts of this invention can be adapted for the closing of other tubular structures at intermediate points as well as near their open ends.

In the course of a surgical operation, a surgeon must often sever one or more blood vessels. It is desirable to provide means for closing the ends of the severed vessels, at least until the end of the operation, to stop bleeding that could interfere with the performance of the operation as well as present unnecessary risks to the patient.

Conventional means for closure consist of ligatures or the like tied about the individual vessels at the desired point of strangulation. The customary technique provides for the separate clamping of each vessel after the incision has been made. After clamping the vessels, a ligature is secured about each vessel providing closure and permitting the removal of the clamps. In some instances a great number of vessels must be severed requiring one or more hours for proper closure at which point the operation may proceed. It will be apparent that an improved technique for closure will not only obviate the excessive expenditures of time by the surgeon and his assistants under conventional practice but also the dangers to the patient inherent in any delay.

As a substitute for the conventional clamping-ligature closure practice, more efficient hemostatic clip systems have been developed. These systems use hemostatic clips housed in a cartridge until they are needed for use, and a clip applicator for removing clips from the cartridge and applying them to the tubular structure. To use, the clips are removed from the cartridge by the scissors-like applicator which has grooves within its jaws for holding the clip, the clip is then placed around the vessel or tube to be closed, and pressure is then applied to the clip to compress it on the tube to effect a seal. Prior to use, the clips are stored in individual compartments within the cartridge, which is designed so that only one clip at a time is removed therefrom.

The type of hemostatic clip systems just described are disclosed in the following U.S. Pat. Nos.: 3,326,216, 3,270,745, 3,439,522, 3,439,523, 3,363,628, and 4,146,130.

One problem with these prior hemostatic clip systems has been in developing a way to keep the clip secured in the cartridge until it is needed for use, and also insuring that it is freely accessible when it is desired to remove it for use. This problem stems from the cartridge being made of plastic while the clip is usually formed of stainless steel or the like. If the clip is tightly tensioned in the cartridge, such as on a central support, it may stick or bind and be difficult to remove from the cartridge. The removal problem is exacerbated if the clip is provided with raised occlusive surfaces on the inside portion thereof. Such surfaces are sometimes desired for insuring that the clip remains securely attached to a blood vessel. Often where such raised occlusive surface is provided plastic will be torn away from the central binding post during removal of the clip from the cartidge and may stick to the clip which is highly undesirable.

Other techniques have been employed to make a more efficient cartridge-clip securing means (see, for example, U.S. Pat. No. 4,146,130). One embodiment therein involves providing a V-shaped clip, the ends of which press against side walls of the cartridge. When it is necessary to remove a clip for use, the applicator is inserted and the sides of the clip are compressed inwardly, giving the clip a U-shape or, more accurately, "barn-shape" and freeing its ends from the side walls. Another embodiment involves having the clips supported loosely on a center post in separate compartments, each of which has a piece of tape extending thereacross to retain the clip. When a clip is desired the applicator is inserted into the compartment, over the opposing legs of the clip and the clip is withdrawn, the tape being displaced to permit such removal.

These hemostatic clip systems, while an improvement over the center post arrangement, have their own disadvantages. In the first embodiment the surgeon must compress the legs of each clip from a V-shape to a barn-shape, a tedious operation. In the second embodiment the clip is somewhat free to move in the compartment and the surgeon's vision of the clip is blocked by the tape. Loading is, therefore, somewhat more difficult than desired and, upon removing the clip, the surgeon must check to see that tape did not stick to the clip.

It is accordingly an object of this invention to provide an improve system for supplying hemostatic clips.

A further object of this invention is to provide an improved cartridge for hemostatic clips in which the clips are not secured to a cartridge central post or to a cartridge side wall.

A further object of this invention is to provide a hemostatic clip cartridge system with an unimpeded view of the clips and where the clips are individually removable with a minimal amount of effort.

Another object of the invention is to provide a cartridge for holding hemostatic clips that is relatively economical to produce.

Another object of the invention is that it allows correct alignment of the clip based on (1) centering of the clip on the apex of the central post in the cartridge and (2) stabilization of the shoulders of the clip by compression by the channel members.

Other objects and advantages of the invention will be apparent from the remaining portion of the description.

BRIEF DESCRIPTION OF THE DRAWINGS

FIG. 1 is a perspective view of the applicator and a clip cartridge according to a preferred embodiment of this invention.

FIG. 2 is a perspective view of a cartridge with clips according to the preferred embodiment.

FIG. 3 is a top plan view of FIG. 2.

FIG. 4 is an enlarged view of the cartridge.

FIG. 5 is a perspective view of a clip.

FIG. 6 is an enlarged sectional view of the clip in the cartridge compartment.

DETAILED DESCRIPTION

Referring to FIG. 1, the clip system according to this invention is illustrated. A plurality of clips 20 are housed in a clip cartridge 10. A clip applicator 30 is provided for removing the clips from the cartridge for application to a blood vessel. The jaws 32 of the applicator are provided with grooves 34 for holding the clip therebetween. As previously disclosed in U.S. Pat. No. 4,146,130, incorporated herein by reference, the applicator has a leaf spring 36 and locking bar mechanism 38 so as to limit the motion of the applicator jaws. This serves to prevent the applicator from compressing the legs 22 of the clip together as it is removed from the cartridge or from dropping the clip once in the jaws. The applicator forms no part of the present invention.

Referring to FIGS. 2, 3 and 4, the construction details of the cartridge 10 according to this invention are illustrated. The cartridge is provided with a plurality of parallel wall dividers 12 that define individual clip compartments 14. In each clip compartment is a center post 16 that extends between the parallel walls, the top portion 18 of which preferably has an inverted V-shape. The apex of the V is located below the top of the parallel walls 12.

Protruding outwardly from the parallel walls into the clip compartment are retaining members 40 that are symmetrically located on either side of the apex of the center post. The channel members are located on both faces of the walls 12 so that in each compartment pairs of channel members face each other. The channel members have an exposed edge portion 42 with approximately semi-circular cross-section.

The channel members 40 extend into the compartment sufficiently that the clips 20 may be secured therebetween. Typically the clips are formed of stainless steel or similar material, while the cartridge and channel members of plastic. Each clip is secured in its compartment by the tension from the channel members until the time for its removal by means of the applicator. When it is necessary to remove the clip, because the channel members are relatively pliant, each clip can be removed from its compartment with minimal effort, and without risk that plastic from the channel members will scrape away and attach to the clip.

Referring to FIG. 6, one advantage of this embodiment is illustrated. Since the clip is secured by the channel members engaging the sides of the clip, it is not necessary to have the legs 22 or bail portion 24 of the clip in tensioned contact with the center post 16. Instead it is only loosely positioned over the post. This and the use of the restricted movement applicator, eliminates the possibility of the clip's legs scraping material away from the center post when the clip is removed. This allows the use of fully preformed clips including, if desired, raised projections 26 along the entire interior opposed portion of its body (see FIG. 5). A fully preformed clip is desirable because it eliminates the need for the surgeon to complete formation of the clip on withdrawing it from the cartridge.

While the channel members 40 are shown as tubular with a constant diameter, it is possible to provide members having an inclination toward the wall of the compartment to ease the engagement of the clip on loading and produce stable retention without excessive fore and aft friction. The correct alignment of the clip insures that the clip is exactly engaged in the applier jaws and not cocked to one side or another, a possibility which exists in the prior art.

While I have shown and described embodiments of this invention in some detail, it wil be understood that this description and illustrations are offered merely by way of example, and that the invention is to be limited in scope only by the appended claims.

What is claimed is:

1. A cartridge for storing and singly dispensing hemostatic clips which are preformed into the proper shape for engagement by a clip applicator, said cartridge having a body portion with a plurality of parallel walls each face thereof defining one side of a clip compartment, means for retaining a clip in each of said clip compartments for permitting dispensing of said clip upon insertion of said clip applicator, said clip compartments being dimensioned to permit reception of said applicator without deformation of said parallel walls, said means for retaining and dispensing the clips comprising a pair of outwardly projecting, opposed channel members extending from each face of each parallel wall into said clip compartments, said opposed channel members positioned and dimensioned so that a clip is releasably compressed therebetween, whereby removal of a clip from one compartment by insertion of the applicator does not release or compress clips in adjacent compartments.

2. The device according to claim 1 wherein said opposed channel members are vertically oriented.

3. The device according to claim 1 wherein the portion of said channel member in contact with the clip is semi-circular in cross-section.

4. The device according to claim 1 wherein said cartridge includes a central support post in each compartment on which said clip is loosely positioned as it is loaded into said compartment and secured by said channel members, said support post insuring easy withdrawal of the clip by the clip applicator.

5. The device according to claim 4 wherein said opposed channel members are located symmetrically about the center of the central support post.

* * * * *